United States Patent [19]

Fleig

[11] Patent Number: 4,610,668
[45] Date of Patent: Sep. 9, 1986

[54] PRESELECTED MULTIPLE DOSAGE SYRINGE

[76] Inventor: John A. Fleig, Rte. 5, Box 3442, Sulphur, La. 70663

[21] Appl. No.: 783,171

[22] Filed: Oct. 2, 1985

[51] Int. Cl.[4] .............................................. A61M 5/00
[52] U.S. Cl. ..................................................... 604/208
[58] Field of Search ................ 604/208, 210, 187, 218

[56] References Cited

U.S. PATENT DOCUMENTS

| | | |
|---|---|---|
| 98,478 | 1/1870 | Eccleston . |
| 201,443 | 3/1878 | Parker . |
| 788,935 | 5/1905 | McKinley et al. . |
| 963,051 | 7/1910 | Kooken . |
| 1,921,034 | 8/1933 | La Marche . |
| 2,358,159 | 9/1944 | Gruetter . |
| 2,502,639 | 4/1950 | Blake ................................ 604/210 |
| 2,792,834 | 5/1957 | Kapelsohn . |
| 2,844,148 | 7/1958 | Raife . |
| 2,875,761 | 3/1959 | Helmer et al. ....................... 604/210 |
| 3,013,435 | 12/1961 | Rodrigues, Jr. . |
| 3,675,492 | 7/1972 | Tejera . |
| 3,730,389 | 5/1973 | Harris, Sr. et al. . |
| 3,749,284 | 7/1973 | Kloehn . |
| 3,780,734 | 12/1973 | Wulff . |
| 3,855,867 | 12/1974 | Roach . |
| 3,881,360 | 5/1975 | Jurado . |
| 3,934,586 | 1/1976 | Easton et al. . |
| 4,050,459 | 9/1977 | Sanchez . |
| 4,073,321 | 2/1978 | Moskowitz . |
| 4,084,730 | 4/1978 | Franke et al. . |
| 4,117,728 | 10/1978 | Johnson . |
| 4,120,205 | 10/1978 | Ripphahn et al. . |
| 4,148,315 | 4/1979 | Berezkin et al. ..................... 604/210 |
| 4,267,846 | 5/1981 | Kontos . |
| 4,444,335 | 4/1984 | Wood et al. . |
| 4,475,905 | 10/1984 | Himmelstrup ....................... 604/208 |

Primary Examiner—John D. Yasko
Attorney, Agent, or Firm—Pravel, Gambrell, Hewitt & Kimball

[57] ABSTRACT

A hypodermic syringe capable of extracting, retaining, and dispensing preselected dosages of fluid medication without dependency on eyesight. The hypodermic syringe has coacting stop means between the barrel and the plunger which may be biased in one direction to positively extract certain quantities and biased in an opposite direction to extract different quantities of fluids.

9 Claims, 2 Drawing Figures

PRESELECTED MULTIPLE DOSAGE SYRINGE

BACKGROUND OF THE INVENTION

This invention relates to a syringe or the like used to extract or dispense pre-selected volumes of fluid through a needle during injections without dependency on eyesight. More particularly, the invention involves syringes utilized in medical applications which can provide a range of set dosages by simple one hand manipulation of the plunger against stop shoulders on the barrel of the syringe.

In time intensive hospital settings multiple dosages of constant volume must be routinely and quickly dispensed. To examine visual calibrations on current syringes for each dosage is time consuming and subject to error. Furthermore, during many injections, the visual attention of the operator and the use of one hand must often be necessarily directed to care and preparation of the patient. A problem therefore exists where selecting a proper dosage requires two hands and/or the visual attention of the operator. A problem also exists where a constant dosage syringe may need to be used to give non-standard dosages. Many syringes adapted to preselected dosages do not allow variable dosages without modification.

Often, the need also arises for individual or unskilled persons to give injections of certain dosages. For example, diabetics find it necessary to give themselves injections of insulin or other medications without medical assistance. Additionally, persons who have sight impediments have difficulty with syringes which are visually calibrated or which do not provide positive nonvisual manipulation to insure that only particular dosages are secured.

A number of devices have attempted to solve these problems. U.S. Pat. No. 4,117,728, discloses a pipette with shoulders for regulating movement of the pipette plunger. However, the stepped shoulders are close together and are only mounted on one side of the guide. This allows little sensitivity for manual, non-visual manipulation and does not provide the fail-safe manual, non-visual certainty necessary in most medical situations.

U.S. Pat. No. 2,792,834 provides an adjustable stop on the barrel of a syringe which appears complicated and costly to manufacture. U.S. Pat. No. 4,475,905, provides a track with numerous turns which must be traversed by a stop on the plunger, traversing these turns would appear to require time consuming and tedious attention by the operator. U.S. Pat. No. 4,267,846 provides a single stop within the barrel of the syringe which does not allow multiple fixed dosages or visual calibration. U.S. Pat. No. 4,084,730 provides a pipette with a complicated step mechanism for use with a detachable piston.

These and other patents provide plunger stop mechanisms which are complicated and expensive to manufacture, difficult to manipulate, and which require visual monitoring to assure that the correct dosage is used. The instant invention solves these problems with a simple stop system allowing multiple fixed dosages to be delivered with speed, fail-safe accuracy, and without visual aid.

It is therefore an object of the invention to provide fail-safe manual manipulation for determination of fixed dosages without the need for visual aid yet provide variable visual calibration when necessary. Another object of the invention is to provide a simple, low cost, disposable syringe. A further object of the invention is to provide a syringe with the above characteristics which can be used by blind and unskilled persons.

SUMMARY OF THE INVENTION

The invention provides a series of stop shoulders along a narrow elongated opening in the barrel of a syringe. The elongated opening may be simply traversed by a protrusion used to control the plunger for full varied volumetric control or constant volumetric control of the syringe. The stop shoulders are arranged in opposing staggered wider portions of the elongated opening. If the protrusion on the plunger is biased to one side of the syringe barrel as it traverses the elongated opening, it will positively engage an appropriate stop shoulder, thus stopping at a preselected dosage with unerring accuracy. Wider portions along the length of the elongated opening gradually vary in width to provide stop shoulders transverse to the elongated opening. The resulting shape of the wider portion of the opening and stop shoulders provides such positive engagement by the protrustion that visual examination of the syringe to check the dosage level is unnecessary. The placement of the protrusion and stop shoulders are such that they coact near the middle of the barrel which allows complete manipulation of the syringe and protrusion with one hand.

BRIEF DESCRIPTION OF THE DRAWINGS

A better understanding of the invention can be obtained when the detailed description of the preferred embodiment set forth below is considered in conjunction with the following drawings, in which.

DETAILED DESCRIPTION OF THE PREFERRED EMBODIMENTS

Figure 1:
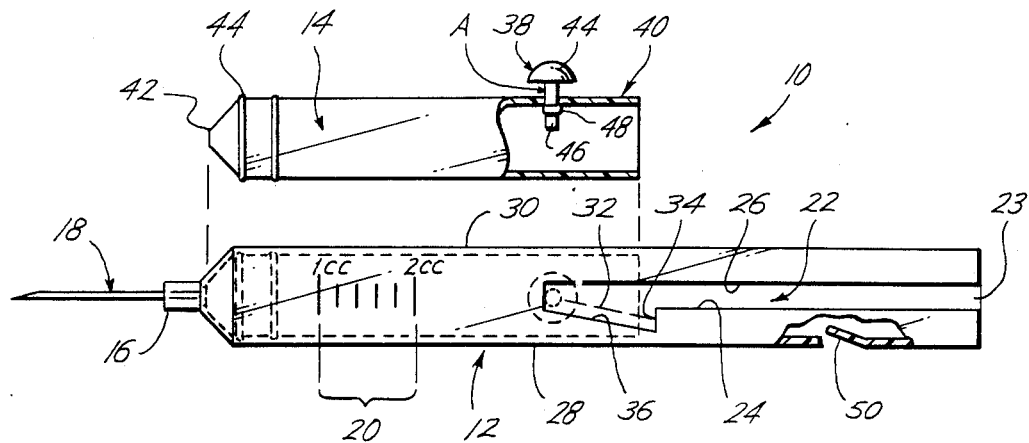
FIG. 1 is a side view of the syringe illustrating the barrel and plunger separately. The barrel features only one stop shoulder along the elongated openings.

FIG. 1 illustrates a hypodermic syringe 10 of the preferred embodiment. The hypodermic syringe 10 is composed of a barrel 12 and plunger 14. The barrel 12 has a lower narrowed end 16 to which a hypodermic needle 18 can be attached for extracting and dispensing fluids, medicines and the like. The barrel 12 had graduated marks 20 along a portion of its length which correspond to the volume of fluid retained in the barrel 12.

Barrel 12 also contains a narrow elongated opening 22 which extends from the mid-portion of the barrel 12 to the upper open end 23 of the barrel 12 opposite the narrowed end 16. The elongated opening 22 has straight sides 24, 26 which are parallel to the sides 28, 30 of barrel 12. The suggested width of the elongated opening might be ⅛". A wider portion 32 is formed in the elongated opening 22 near the mid-portion of the syringe body 12. Wider portion 32 tapers from a narrow point at one end of the wider portion nearest the narrow end 16 of barrel 12 to a wider point at the opposite end of the wider portion nearest the upper open end 23 of barrel 12. The suggested width of the widest portion in the elongated opening may be ⅜". At the widest point of wider portion 32, a stop shoulder 34 is formed by a linear edge of the wider portion positioned transverse to the sides 24, 26 of elongated opening 22. Edge 36 of wider portion 32 extends from the narrow point to the widest point of wider portion 32 and generally forms a straight edge to provide a smooth transition surface along which protrusion 38 can slide to engage stop shoulder 34.

Plunger 14 consists of a plunger barrel 40 and rubber tip 42 which conform to the inner portion of barrel 12 so that fluids can be retained between sealing edge 44 of plunger tip 42 and the narrow end 16 of barrel 12. Plunger 14 is free to rotate or move oxially within barrel 12. Note that barrel 12 is preferably made of transparent material so that seal 44 can be seen through barrel 12 as it passes calibration marks 20.

Plunger barrel 40 is fitted with a protrusion 38 to allow control of the plunger from a position outside barrel 12. Protrusion 38 is formed of a top button 44 and shaft 46. The top button 44 is wider than shaft 46 for easier manipulation by the operator. The diameter of shaft 46 is sized such that it will fit within elongated opening 22. Shaft 46 has a ridge 48 which when inserted into an appropriate hole in plunger barrel 40 secures shaft 46 in the hole. Button top 44 is removed a certain distance from the outer surface of plunger barrel 40 to provide space A. Space A should be sufficient to allow clearance of the barrel 12 when plunger 14 is inserted in barrel 12 and shaft 46 is positioned within the elongated opening 22. Note that lip 50 is provided in barrel 12 so that once the plunger 14 is inserted into the barrel past lip 50, it cannot easily be removed. Lip 50 is formed by a portion of the side 28 of barrel 12. In operation, plunger 14 is inserted into barrel 12 past lip 50 so that shaft 46 of protrusion 38 fits within elongated opening 22. Protrusion 38 is passed to the end of elongated opening 22 nearest the narrow end 16 of barrel 12. When the protrusion 38 is in this position in elongated opening 22, plunger tip 42 should engage narrow end 16 of barrel 12 to insure that no fluid is in the syringe. This will be referred to as the start position of the plunger.

Stop shoulder 34 of wider portion 32 may be positioned at any point along elongated opening 22 which corresponds with the amount of fluid required to be contained within the barrel 12 without necessity of visual aid. To utilize the syringe 10, the operator simply grasps the barrel 12 with one hand and controls protrusion 38 with the thumb of that hand. Protrusion 38 is then moved from the start position toward the open end 23 of barrel 12, thus filling the space between plunger tip 42 and narrow end 16 of barrel 12 with fluid when needle 18 is immersed in fluid. If protrusion 38 is biased by the operator toward side 26 of elongated opening 22, the syringe may be filled with any volume of fluid desired. However, if protrusion 38 is biased toward side 28 of barrel 12 so that it follows tapered surface 36 of wider portion 32 as the plunger 14 draws fluid into barrel 12, shaft 46 of protrusion 38 will positively engage stop shoulder 34 and limit the amount of fluid withdrawn into barrel 12. Because of the ease with which protrusion 38 can be biased against the sides of the elongated opening 22 and wider portion 32, and the positive nature of stop shoulder 34 of wider portion 32, the withdrawal of a specific amount of fluid can be accomplished with complete confidence and without visually examining the syringe.

Figure 2:
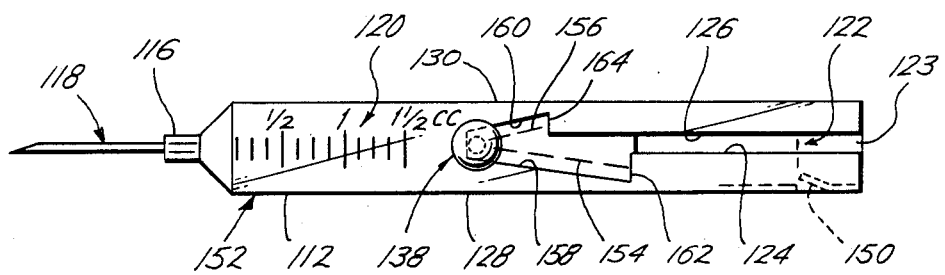
FIG. 2 illustrates an alternative embodiment of the syringe with two stop shoulders along the elongated opening.

An alternative embodiment of the hypodermic syringe of the instant invention is illustrated in FIG. 2. The alternative embodiment is similar to the preferred embodiment and like numbers are used to identify like parts with the addition of 100 to each identifying number. For example, the alternative embodiment is comprised of a barrel 112 with narrow end 116 adapted to accommodate needle 118 and an open end 123. Calibrations 120 on barrel 112 identify the amount of fluid for a given position of the plunger (not shown) within the barrel 112. Barrel 112 has sides 128, 130 with a lip 150 inside barrel 112 to prevent the plunger from easily sliding out of barrel 112 once inserted. Barrel 112 has an elongated narrow opening 122 with straight sides 124, 126 which are parallel to the sides 128, 130 of barrel 112, all similar to the preferred embodiment.

In contrast to the preferred embodiment, the alternative embodiment 152 has two wider portions 154, 156 staggered opposite each other along narrow elongated opening 122. Wider portion 154 and 156 have narrow points and wider points similar to wider portion 32 of the preferred embodiment in FIG. 1. Wider portions 154, 156 have linear tapers 158, 160 between the respective narrow and the wider points, and have stop shoulders 162, 164 respectively positioned transverse to the sides 124, 126 of elongated opening 122. Note that the wider portions 154, 156 are positioned on opposite sides of elongated opening 122 and that stop shoulders 162 and 164 are positioned at different distances from the narrow end 116 of barrel 112.

In operation of the alternate embodiment, protrusion 138 can be biased by the operator's thumb toward side 130 of barrel 112 as it is moved from the start position along narrow opening 122. This forces protrusion 138 to move along tapered edge 160 of wider portion 156 until it engages stop shoulder 164. Thus, a certain predetermined volume, determined by the distance between stop shoulder 164 and narrow end 116 of barrel 112, is allowed to enter the barrel 112 of syringe 152. In similar fashion, protrusion 138 may be biased toward side 128 of barrel 112 with the operator's thumb or other digits such that as the plunger (not shown in FIG. 2) is withdrawn, protrusion 138 will engage stop shoulder 162. Thus, a second greater quantity of fluid may be drawn into the barrel 112 of the syringe 152. Alternatively, protrusion 138 may be guided by the operator as it moves along opening 122 such that it bypasses stop shoulder 162 or 164 so that varying quantities of fluid may enter the barrel 112 of syringe 152 as indicated by calibrations 120.

The foregoing disclosure and description of the invention are illustrative and explanatory and various changes in size, shape and materials as well as in the details of the illustrated construction may be made without departing from the spirit of the invention. All such changes and variations are contemplated as falling within the scope of the appended claims.

I claim:

1. A manually operated hypodermic syringe for extracting, retaining, and dispensing preselected dosages of fluid through a needle during injections comprising:
   a. a barrel means for retaining fluid adapted at one end to allow the passage of fluid;
   b. manually operable plunger means adapted to fit within the barrel means to control fluid in the barrel; and
   c. stop means coacting between the barrel and the plunger which may be biased in one direction to extract certain preselected quantities of fluid without visual monitoring and biased in the opposite direction to extract different quantities of fluid.

wherein said stop means comprises a portion of the barrel having an elongated opening with a plurality of wider portions in which each wider portion is successively staggered on opposite sides of the elongated opening along its length and each wider portion of the opening forms a stop shoulder on the barrel means.

2. The syringe of claim 1 in which the elongated opening, between wider portions, has linear parallel sides along its length.

3. The syringe of claim 1 in which the stop means further comprises a protrusion on the plunger means for controlling the plunger means by traversing the elongated opening and by selectively engaging stop shoulders on the barrel means.

4. The syringe of claim 3 in which each wider portion in the opening tapers from a narrow point at one end of the wider portion nearest the fluid passing end of the barrel means to a wider point at the opposite end of the wider portion in order to provide a positive stop shoulder which can be unmistakably detected by the operator's sense of touch without visual aid.

5. The syringe of claim 4 in which the widest point of each wider portion of the opening in the barrel is proximate to the stop shoulder.

6. The syringe of claim 5 in which the stop shoulder is formed by a linear edge of the barrel which forms part of each wider portion of the elongated opening in the barrel, said linear edge being oriented generally traverse to the axis of the elongated opening.

7. The syringe of claim 3 in which the elongated opening is of sufficient length and orientation to allow the plunger to dispense substantially all the liquid retained in the barrel and to allow the protrusion on the plunger to move in a linear direction along the axis of the barrel during extraction and dispensing of liquids.

8. The syringe of claim 7 in which the barrel is calibrated so that volumes of fluid retained in the barrel may be determined without engaging and without reference to the stop means.

9. The syringe of claim 3 in which a first stop means is positioned near the middle of the length of the barrel so that the upper portion of the barrel can be grasped by the hand and the protrusion on the plunger can be manipulated by the thumb of the same hand.

* * * * *

UNITED STATES PATENT AND TRADEMARK OFFICE
CERTIFICATE OF CORRECTION

PATENT NO. : 4,610,668

DATED : Sep. 9, 1986

INVENTOR(S) : JOHN A. FLEIG

It is certified that error appears in the above-identified patent and that said Letters Patent is hereby corrected as shown below:

Column 2, line 50 - Delete the word [had] and insert --has--.

Column 4, line 68 - Delete the period [.] and insert a comma, -- , --.

Signed and Sealed this

Sixth Day of January, 1987

Attest:

DONALD J. QUIGG

*Attesting Officer*  *Commissioner of Patents and Trademarks*